US00PP13321P2

(12) United States Plant Patent
Sorensen

(10) Patent No.: US PP13,321 P2
(45) Date of Patent: Dec. 3, 2002

(54) OSTEOSPERMUM PLANT NAMED 'AKVARZA'

(75) Inventor: Carl Aksel Kragh Sorensen, Aabyhøj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/968,315

(22) Filed: Sep. 30, 2001

(51) Int. Cl.[7] ..... A01H 5/00

(52) U.S. Cl. ..... Plt./360
(58) Field of Search ..... Plt./360

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Osteospermum plant named 'Akvarza', characterized by its uniformly mounded and outwardly spreading plant habit; freely branching growth habit; full and dense plants; freely flowering habit; green and pale yellow variegated foliage; and white-colored ray florets and light gray-colored disc florets.

1 Drawing Sheet

BACKGROUND OF THE INVENTION

The present Invention relates to a new and distinct cultivar of Osteospermum plant, botanically known as *Osteospermum ecklonis,* and hereinafter referred to by the name 'Akvarza'.

The new Osteospermum is a product of a planned breeding program conducted by the Inventor in Aabyhøj, Denmark. The objective of the breeding program is to create new Osteospermum cultivars with uniform plant habit and interesting leaf and floret colors.

The new Osteospermum is a naturally-occurring branch mutation of the *Osteospermum ecklonis* cultivar Cape Daisy Lusaka, disclosed in U.S. Plant Pat. No. 10,337. The new Osteospermum was discovered and selected by the Inventor as a single plant within a population of plants of the cultivar Cape Daisy Lusaka during the winter of 1998 in a controlled environment in Aabyhøj, Denmark. The selection of this plant was based on its unique variegated foliage.

Asexual reproduction of the new Osteospermum by vegetative tip cuttings was first conducted in Aabyhøj, Denmark during the spring of 1998. Asexual reproduction by cuttings has shown that the unique features of this new Osteospermum are stable and reproduced true to type in successive generations.

SUMMARY OF THE INVENTION

The cultivar Akvarza has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Akvarza'. These characteristics in combination distinguish 'Akvarza' as a new and distinct Osteospermum:

1. Uniformly mounded and outwardly spreading plant habit.

2. Freely branching growth habit; full and dense plants.

3. Freely flowering habit.

4. Green and pale yellow variegated foliage.

5. White-colored ray florets and light gray-colored disc florets.

The new Osteospermum are most similar to plants of the parent, the cultivar Cape Daisy Lusaka. In side-by-side comparisons conducted in Encinitas, Calif., plants of the new Osteospermum differed from plants of the cultivar Cape Daisy Lusaka in the following characteristics:

1. Plants of the new Osteospermum were more compact than plants of the cultivar Cape Daisy Lusaka.

2. Leaves of plants of the new Osteospermum were green and pale yellow variegated whereas leaves of plants of the cultivar Cape Daisy Lusaka were solid green in color.

Plants of the new Osteospermum differ primarily from plants of the cultivar Akvarlu, U.S. Plant Patent application filed concurrently with this application, in ray floret coloration.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colors in the photographs may differ from the color values cited in the detailed botanical description which accurately describe the colors of the new Osteospermum.

The photograph at the top of the sheet comprises a side perspective view of three typical flowering plants of 'Akvarza' grown in a 22-cm container.

The photograph at the bottom of the sheet is a close-up view of typical leaves, inflorescences and inflorescence buds of 'Akvarza'.

DETAILED BOTANICAL DESCRIPTION

In the following description, color references are made to The Royal Horticultural Society Colour Chart except where general terms of ordinary dictionary significance are used. The aforementioned photographs, following observations and averaged measurements describe plants grown during the late winter and early spring in Encinitas, Calif., in polyethylene-covered greenhouses and under conditions which approximate those generally used in commercial Osteospermum production. Three rooted cuttings were planted in 22-cm containers and pinched once. During the production of the plants, day temperatures were about 24° C., night temperatures were about 19° C., and light levels were about 4,000 foot-candles. Measurements and numerical values represent averages of typical flowering plants about 18 weeks after planting.

Botanical classification: *Osteospermum ecklonis* cultivar Akvarza.

Parentage: Naturally-occurring branch mutation of the *Osteospermum ecklonis* cultivar Cape Daisy Lusaka, disclosed in U.S. Plant Pat. No. 10,337.

Propagation:

*Type*.—Terminal cuttings.

*Time to initiate rooting*.—About 10 days at 18° C.

*Time to develop roots*.—About 24 days at 18° C.

*Root description*.—Fibrous and well-branched.

Plant description:

*Appearance*.—Perennial herbaceous container and garden plant. Uniformly mounded plant habit; upright to outwardly spreading. Freely branching, about 10 to 11 lateral branches develop after pinching; dense and full plants. Moderately vigorous growth habit.

*Plant height*.—About 42 cm.

*Plant width or area of spread*.—All three plants, about 65 cm; individual plants, about 29 cm.

*Lateral branches*.—Length: About 37 cm. Diameter: About 4.5 mm. Internode length: About 1.5 cm. Aspect: Upright to outward. Strength: Strong, but tallest lateral branches may tend to bend with the weight of the inflorescences. Texture: Glabrous. Color: 144C.

*Foliage description*.—Arrangement: Alternate; simple. Number of leaves per lateral branch: About 18. Length: About 4.5 cm. Width: About 1.7 cm. Shape: Elliptic. Apex: Broadly acute. Base: Attenuate. Margin: Nearly entire with occasional tiny serrations. Venation pattern: Pinnate. Texture: Coarse, leathery, glandular and glabrous. Color: Young foliage, upper and lower surfaces: Center, 147B, surrounded by 10D to the margins. Fully expanded foliage, upper surface: Center, 147A to 147B, surrounded by 10D to the margin. Fully expanded foliage, lower surface: Center, 147B to 147C, surrounded by 10D to the margin. Venation, upper and lower surfaces: 147C. Petiole: Length: About 1.5 cm. Diameter: About 4 mm. Texture, upper and lower surfaces: Glabrous. Color, upper and lower surfaces: 147C.

Inflorescence description:

*Appearance*.—Terminal and axillary inflorescences held above and beyond the foliage on moderately strong peduncles. Composite inflorescence form, radially symmetrical, with ligulate-shaped ray florets and disc florets massed at the center; ray and disc florets arranged acropetally on a capitulum. Inflorescences persistent. Inflorescences face upright or outward.

*Flowering response*.—Plants flower continuous and freely from the spring through the fall.

*Postproduction longevity*.—Inflorescences maintain good color and substance for about one week on the plant when grown in an outdoor environment.

*Quantity of inflorescences*.—Freely flowering; at one time, about 100 open inflorescences and buds per plant.

*Fragrance*.—Not detected.

*Inflorescence bud (at stage of showing color)*.—Length: About 2 cm. Diameter: About 8 mm. Shape: Ovoid. Color, ray florets, lower or outer surface: 150B.

*Inflorescence size*.—Diameter: About 7.5 cm. Depth (height): About 2 cm. Disc diameter: About 8 mm. Receptacle diameter: About 1.8 cm. Receptacle height: About 1.1 cm.

*Ray florets*.—Length: About 4 cm. Width: About 8 mm. Shape: Ligulate. Apex: Rounded to slightly emarginate. Base: Acute. Margin: Entire. Texture: Satiny. Orientation: Initially upright to about 65° from vertical. Number of ray florets per inflorescence: About 21 in a single whorl. Color: When opening, upper surface: 155A. When opening, lower surface: 150C. Fully opened, upper surface: 155D. Fully opened, lower surface: Ground color, 155A, with longitudinal stripe, 4C, that broadens towards the apex.

*Disc florets*.—Shape: Tubular, elongated. Apex: Five-pointed. Length: About 9 mm. Width: At apex: About 2 mm. At base: About 1 mm. Number of disc florets per inflorescence: About 70. Color: Immature: 156A. Mature: Apex: 156A to 155B. Mid-section and base: 155B.

*Phyllaries*.—Length: About 1 cm. Diameter: About 2 mm. Shape: Linear. Apex: Acute. Base: Fused. Margin: Entire. Texture: Slightly coarse with tiny hairs. Number per inflorescence: About 21 in a single whorl. Color, upper and lower surfaces: Center, 147B, surrounded by 4C to the margin.

*Peduncles*.—Length, terminal peduncle: About 8 cm. Length, second peduncle: About 11 cm. Length, third peduncle: About 10.5 cm. Diameter: About 1.5 mm. Angle: Terminal peduncles, erect; secondary and tertiary peduncles, about 45° from vertical. Strength: Moderate, tend to bend with weight of inflorescences. Texture: Coarse with tiny scattered short hairs. Color: 144D.

*Reproductive organs*.—Androecium: Present on disc florets only. Stamen number: Five per floret; fused around style. Anther shape: Oblong. Anther size: About 2 mm by 1 mm. Anther color: 14A. Pollen amount: Scarce. Pollen color: 14A. Gynoecium: Present on both ray and disc florets. Pistil number: One per floret. Pistil length: About 8 mm. Stigma shape: Two-parted. Stigma color: 155A. Style length: About 5 mm. Style color: 155A. Ovary color: 144D.

*Seed*.—Seed production has not been observed.

Disease/pest resistance: Resistance to pathogens and pests common to Osteospermums has not been observed on plants grown under commercial greenhouse or outdoor conditions.

Temperature tolerance: Plants of the new Osteospermum have been observed to tolerate temperatures from 4° to 32° C.

It is claimed:

1. A new and distinct cultivar of Osteospermum plant named 'Akvarza', as illustrated and described.

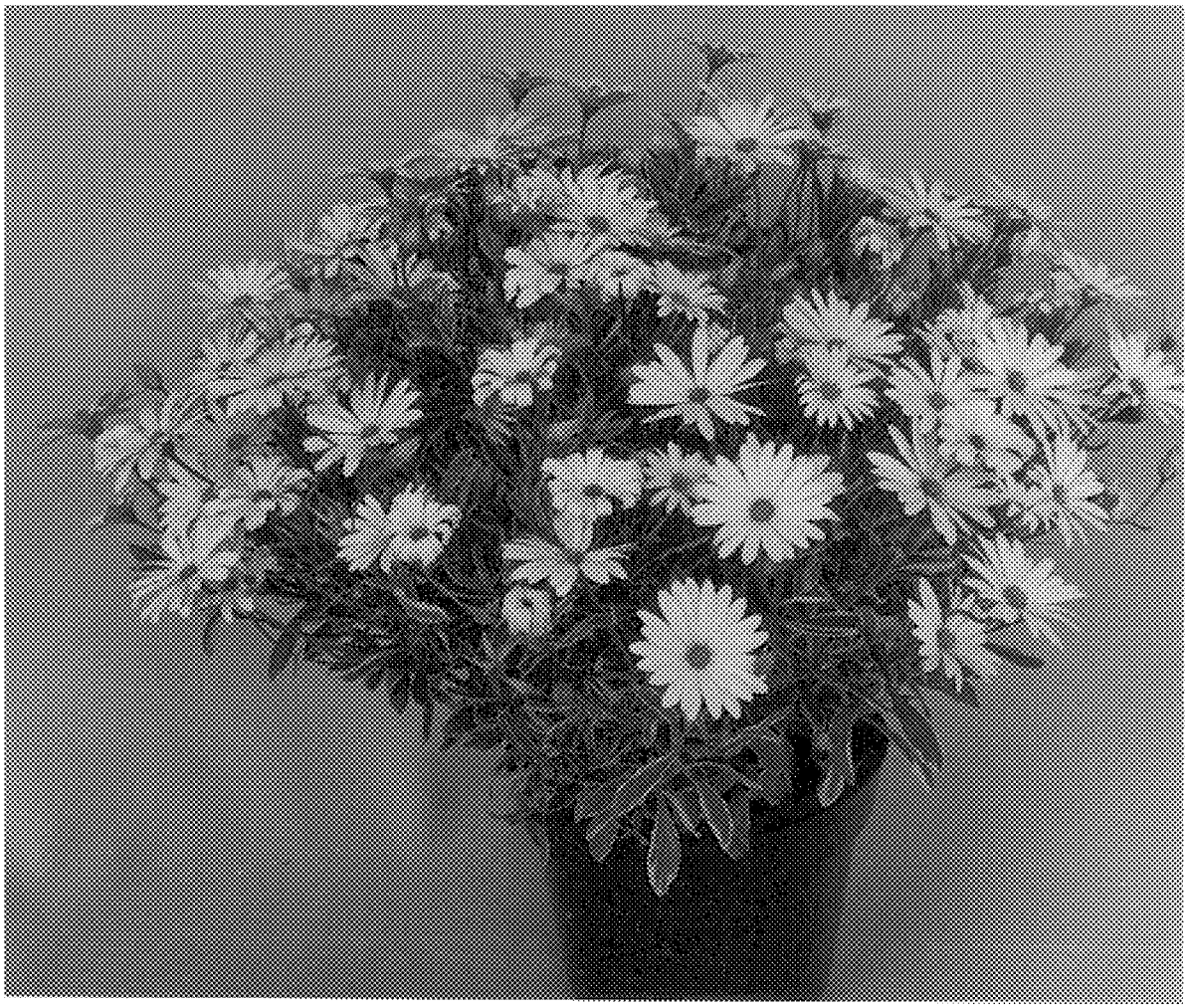
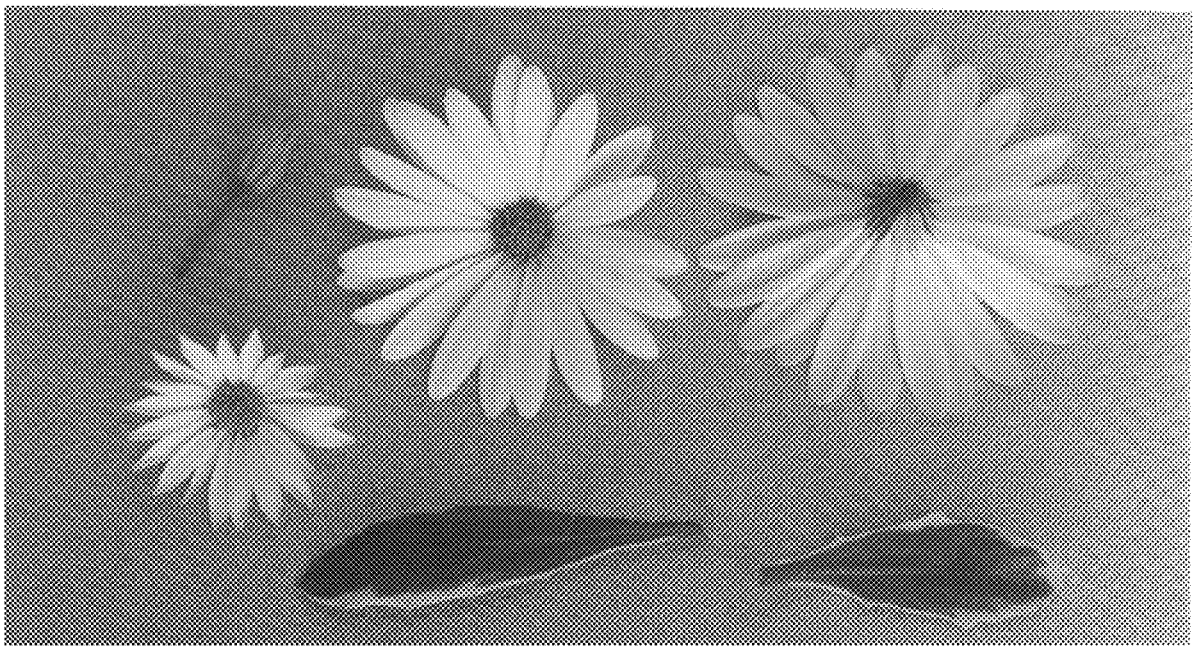

* * * * *